United States Patent [19]
Klinzing et al.

[11] Patent Number: 5,540,374
[45] Date of Patent: Jul. 30, 1996

[54] BONE STAPLER CARTRIDGE

[75] Inventors: William P. Klinzing, St. Paul, Minn.; Barry W. Robole, Woodville, Wis.

[73] Assignee: Minnesota Mining and Manufacturing Company, St. Paul, Minn.

[21] Appl. No.: 319,293

[22] Filed: Oct. 6, 1994

[51] Int. Cl.⁶ .................................................. A61B 17/068
[52] U.S. Cl. ........................ 227/176.1; 227/19; 227/109
[58] Field of Search ............................ 227/175.1, 176.1, 227/178.1, 19, 120, 119, 109

[56] References Cited

U.S. PATENT DOCUMENTS

| | | |
|---|---|---|
| Re. 33,362 | 10/1990 | Mongeon et al. . |
| 4,414,967 | 11/1983 | Shapiro . |
| 4,500,025 | 2/1985 | Skwor . |
| 4,527,726 | 7/1985 | Assell et al. . |
| 4,569,469 | 2/1986 | Mongeon et al. . |
| 4,648,541 | 3/1987 | Mongeon . |
| 5,163,598 | 11/1992 | Peters et al. ............................. 227/19 |

*Primary Examiner*—Scott A. Smith
*Attorney, Agent, or Firm*—Gary L. Griswold; Walter N. Kirn; Jeffrey J. Hohenshell

[57] ABSTRACT

A cartridge for use in a stapler for driving staples during orthopedic surgery is described. The cartridge has a case comprising a first wall and side walls projecting from this first wall. The cartridge has inner guide surfaces intended to guide the movement of staples when they are ejected by the stapler, and these preferably include the top of extended projections from a spacer element which is snap fit to the case. Within the case are a stack of staples supported on a follower which pushes on the side of the stack of staples so as to sequentially present each one in turn in a position to be ejected by the stapler. The follower is centered and slidably mounted on a guidepost which helps the follower resist any tendency for misalignment of the follower within the case.

18 Claims, 9 Drawing Sheets

5,540,374

BONE STAPLER CARTRIDGE

TECHNICAL FIELD

This invention relates to staple cartridges used in devices for driving staples, and more particularly to staple cartridges used in orthopedic bone staplers.

BACKGROUND

Certain orthopedic procedures are known where sections of bone are fixed together, or where prosthetic devices are fixed to bone. In recent years bone staplers have been introduced which are capable of driving hardened (e.g. titanium) staples into bone to accomplish these ends.

U.S. Pat. Nos. 4,500,025 and 4,527,726 describe devices suitable for stapling bone during an orthopedic surgical procedure. The disclosures of those two patents are hereby incorporated by reference in their entirety. Those patents describe a bone stapler with a removable staple cartridge which precludes leaving a staple in the stapler that could be inadvertently driven after the cartridge is removed. Such a cartridge includes a case that comprises guide walls defining an inner surface at the end of a stack of staples opposite a follower, and side walls projecting normal to the inner surface. Opposed openings in the inner surface align with a passageway for a staple driver when the cartridge is inserted into the stapler. Because all of the staples remain within the cartridge until they are driven, the user can be assured that all the staples are removed from the stapler when the cartridge is removed.

U.S. Pat. No. 4,569,469 and Reissue Patent No. 33,362 (each of which are also incorporated by reference) describe a bone stapler cartridge that is less expensive to manufacture and significantly easier to use than the devices described in U.S. Pat. Nos. 4,500,025 and 4,527,726. While this device operates suitably, improvements may be made to enhance the design of the bone stapler cartridge. A review of the factors affecting the design and construction of a bone stapler cartridge highlight the advantages of the present invention.

A bone stapler according to the prior art includes a staple driver that is powered pneumatically. The staple driver provides a relatively large force that expels the staples from the staple cartridge and into bone tissue. This requires careful alignment of the staples within the staple cartridge, and the staple cartridge within the staple driving device. Any binding, skewing or misalignment of the staples within the cartridge may result in undesirable results such as malformed staples, binding of the bone stapler or destruction of the staple cartridge housing.

The variety of orthopedic surgical procedures which call for a bone staple result in a need for a variety of bone staple sizes. Typically, the same staple driving device will be used to drive a variety of different sized staples. Further, it is desirable to reduce to a minimum the number of different cartridge case sizes for which molds are required and parts have to be inventoried. For example, it is desirable that the same width of cartridge be used with all the staples of a particular width but with different leg lengths. This has been difficult to achieve in practice, however; as staples with short leg lengths have a potential to jam within a cartridge designed to accommodate the same width staples with longer leg lengths.

One known solution to this dilemma is embodied in staple cartridges sold by 3M Company of St. Paul, Minn. as e.g. Cat. No. 7615 bone stapler cartridges. These cartridges are constructed with a spacer block within an outer case, both pieces formed as individual polymeric moldings which are then fused or solvent welded to each other. The spacer block then can help guide the pointed legs of the generally U-shaped staples toward the staple outlet of the driver.

Several problems are associated with the fusing or solvent welding step during assembly. First, a solvent has the potential to mar, deform, streak, misalign and/or weaken the polymeric housing elements thereby increasing the incidents of defective housings encountered during assembly and construction, and increasing the risk that the staples will be exposed to the adhesive. Second, the adhesive requires a dwell time that increases the time required to construct a bone staple cartridge. Third, capillary action can carry the typically thin solvent to areas where it is unwanted.

While defective cartridges do not reach the consumer, the great care and attention to detail taken during inspection procedures are time intensive. As a result, prior art procedures for assembly of a bone stapler cartridge have the capacity for improvement.

Followers according to present designs also leave room for improvement in providing even, reliable support for the stack of staples within the cartridge to avoid undesirable consequences such as jamming. The follower should a) be quickly and easily assembled without the use of adhesives or solvents, b) move the stack of staples into position robustly, and c) support each staple reliably during ejection.

SUMMARY OF THE INVENTION

The present invention provides a bone staple cartridge which: (1) is less difficult to manufacture than prior art bone staple cartridges, (2) is capable of use with a variety of bone staple sizes while resisting misalignment of the bone staples relative to the cartridge; (3) optionally includes a spacer with a guide surface for use with smaller sized staples within a larger sized cartridge (e.g. a cartridge which may be used with staples of a similar width, but with a different leg length), which spacer may be placed substantially adjacent the side walls of the cartridge so that the cartridge resists staple binding between a side wall and the spacer, and (4) optionally may be assembled without the use of an adhesive.

According to the present invention, there is provided a cartridge adapted for use in a stapler for driving staples. "Staples" is generally referring to a hardened metal construct having a central portion having a pair of ends and a leg portion projecting from each of the ends, with the leg portions having sharpened distal ends. They are conveniently U-shaped.

The cartridge interacts with a stapler that has a stapler housing having a passageway extending from an inlet opening to an outlet opening, the passageway guiding a single staple moved from the inlet to the outlet opening with the distal ends of its legs leading. The stapler has a driver having a staple driving end portion for engaging a staple. The driver is movable between (1) a load position with the driver spaced from the inlet opening so that one of the staples may be positioned in the passageway, and (2) an eject position at which the staple driving end portion of the driver pushes the staple out the outlet opening.

The stapler also has a drive means adapted to be manually activated for propelling the driver along the passageway from the load to the eject position to move the staple from the inlet to the outlet opening. The stapler housing includes surfaces adapted to releasably receive the cartridge according to the present invention.

The cartridge has a case comprising a first wall and side walls projecting from this first wall. The cartridge has inner guide surfaces intended to guide the movement of staples, and opposed openings situated such that, when the cartridge is received by the stapler, the guide surface and opposed openings define a portion of the stapler passageway discussed above so that the driver can be moved through the opposed openings and adjacent the guide surfaces between the load and eject positions.

Within the case is a stack of staples supported on a follower which pushes on the side of the stack of staples opposite the first wall. The follower is movable within the case with the stack of staples as they are ejected sequentially. The follower is biased by a spring that urges the follower and the stack of staples toward the first wall so that the staples can be ejected. The follower has a bearing surface, preferably a hole within an enlarged boss, adapted to slidably engage a guidepost within the case. This helps the follower resist any tendency for misalignment of the follower within the case.

The cartridge also has some means for releasably retaining the case in engagement with the stapler housing. Conveniently, this may be a rotatable wing pin received within a complementary hole in the stapler.

Preferably, the cartridge according to the present invention further includes a spacer having projections with guide surfaces substantially adjacent the side walls for guiding a staple through one of the opposed openings. Most preferably, this spacer has a snap-fit means for attaching the spacer to a second wall, which means that the attachment is free of adhesive. By "snap-fit means", what is meant is a mode of clasping which involves a portion, such as a hook, on one of the parts to be clasped which, when pressed against a portion, such as a recess on the other part, is capable of, and indeed adapted for, a-resilient deflection which allows the parts to interact and thereafter resist being separated.

Another optional feature of the invention is a spacer which has a pair of upright projections which support the staple during ejection. Because the spacer is snap-fit into place, these projections can be mounted very close to the side walls of the case. A further feature of the invention is the staple follower which is supported and guided by a guidepost so as to provide a more even support to the staples within the case.

DETAILED DESCRIPTION

Figure 1:
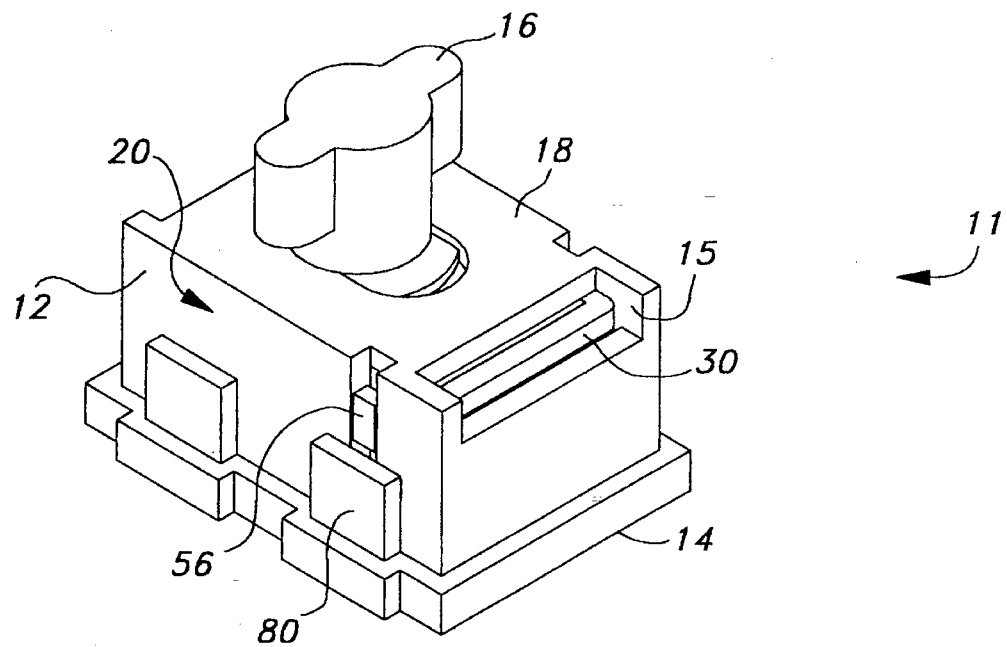
FIG. 1 is a perspective view of a staple cartridge according to the present invention.
Figure 11:
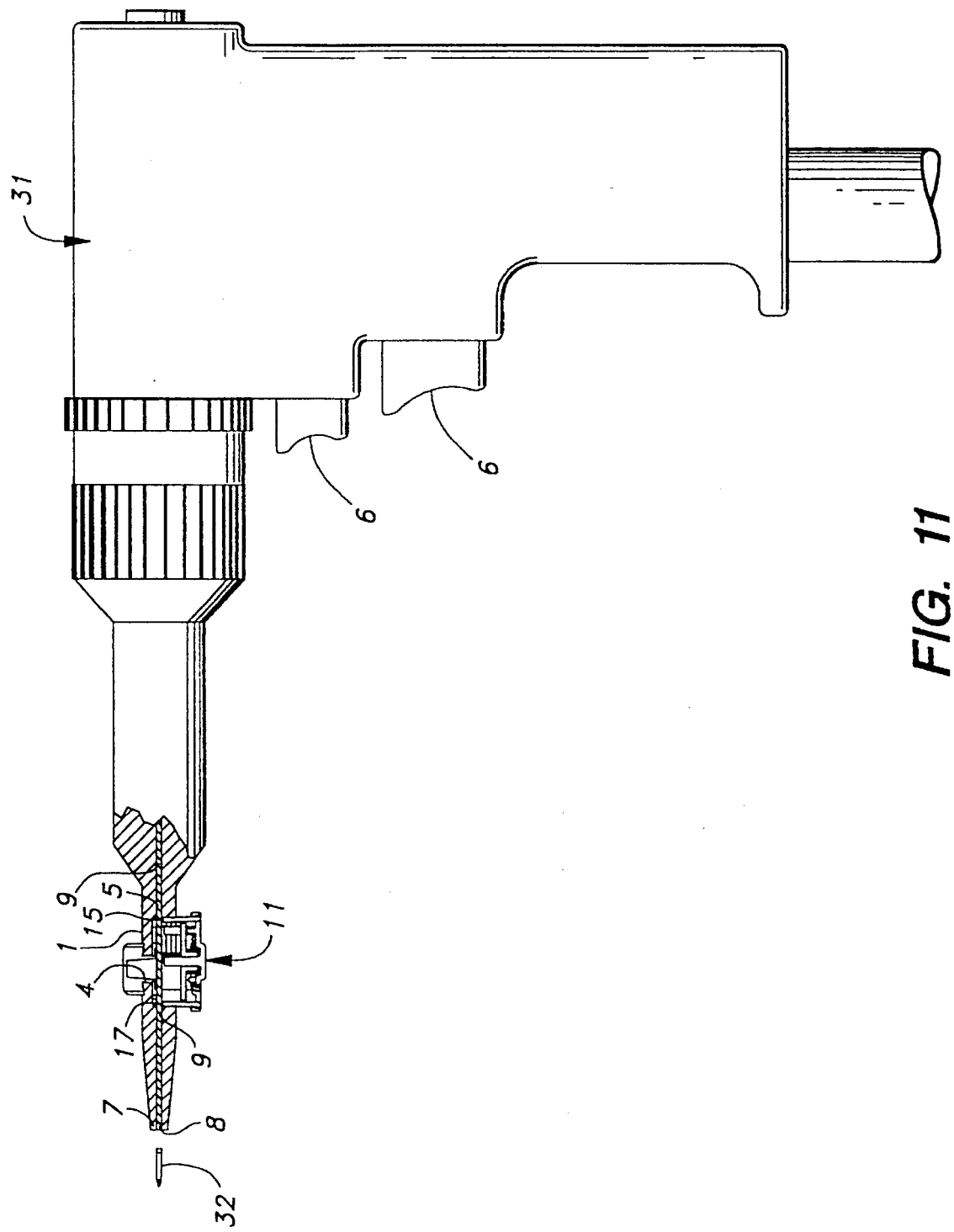
FIG. 11 is a side, partial cross-section view of the staple cartridge of FIG. 1 attached to a staple driving device.

Referring now to FIGS. 1 and 11, a staple cartridge 11 according to the present invention is depicted. The cartridge 11 is adapted for use with a bone stapler 2, such as, for example, the bone stapler disclosed in U.S. Pat. No. 4,569,469 and its Reissue No. 33,362 (the entire contents of each which are herein expressly incorporated by reference). When the cartridge 11 is attached to the bone stapler 2, the bone stapler 2 is designed to sequentially drive a single bone staple from a stack of staples 28. Each of the staples comprise a central portion 30 having a pair of ends and a leg portion 32 projecting from each of the ends. The leg portions 32 have distal ends 34 which are preferably sharp for piercing tissue such as bone.

Referring to FIG. 11, the bone stapler 2 comprises a stapler housing 3 having a passageway extending from an inlet opening 5 to an outlet opening 7. The passageway is designed to guide a single staple moved from the inlet 5 to the outlet 7 opening with the distal ends 34 of its legs 32 leading. The bone stapler 2 also includes a driver 9 having a staple driving end portion 8 adapted to engage a staple from the stack 28 of staples. The driver 9 is mounted for movement between a) a load position with the driver 9 spaced proximally (toward the user's hand that grasps the pistol grip of the housing) from the inlet opening 5 so that one of the staples may be positioned in the passageway, and b) an eject position at which the staple driving end portion 8 of the driver 9 pushes the staple out the outlet opening 7 (see FIG. 11).

A drive means is present which is adapted to be manually activated for propelling the driver 9 along the passageway from the load to the eject position to move the bone staple from the inlet 5 to the outlet opening 7. The drive means is activated by pushbuttons 6. The drive means is disclosed in U.S. Pat. No. 4,569,469 and its Reissue No. 33,362 (the entire contents of each which are herein expressly incorporated by reference). The stapler housing 3 also includes surfaces 4 adapted to receive the cartridge 11.

Figure 2:
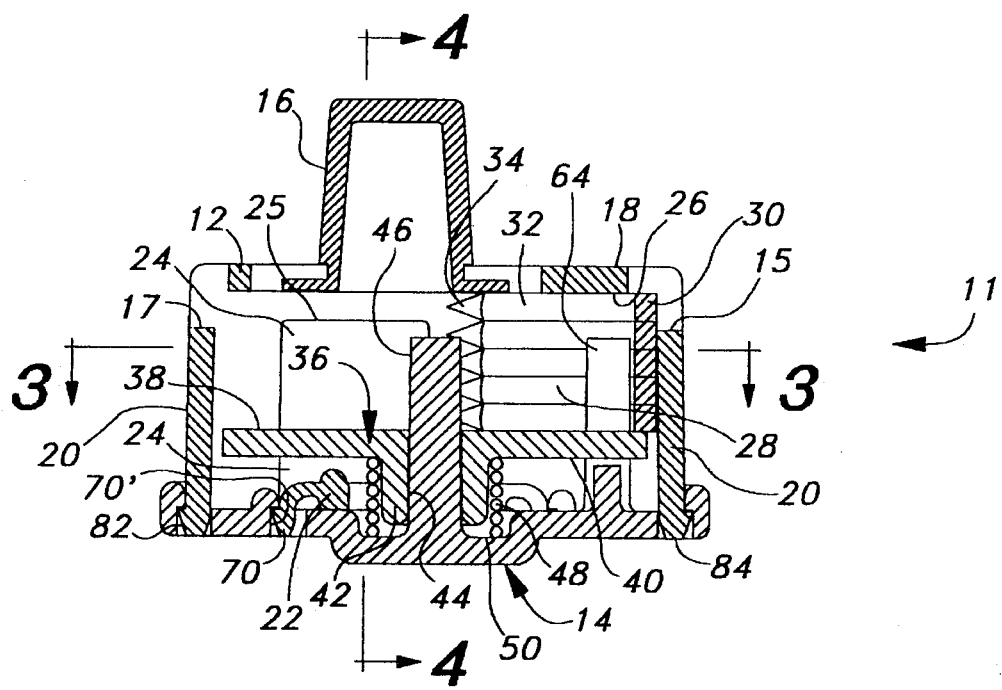
FIG. 2 is a cross-section view of the cartridge of FIG. 1, taken approximately along a vertical plane.

Referring now to FIG. 2, a cross section side view of the staple cartridge 11 is depicted. The cartridge 11 includes a case 12 including a first wall 18, side walls 20 projecting from the first wall 18, a second wall 14, and a locking member 16. The second wall 14 is attached to the side walls 20 by a snap-fit which is described in greater detail below in conjunction with an optional spacer 22 of the cartridge 11. The component which may be used to form the second wall 14 is illustrated in greater detail in FIGS. 12 and 13.

Snap-fitted to the second wall 14 is an optional spacer 22. The component which may be used as the spacer 22 is best seen in FIGS. 7 and 14–16. The spacer 22 allows the basic cartridge 11 to be used with a plurality of bone staple sizes which have the same staple width. Typical staple width for bone staplers include seven and thirteen millimeter widths. For example, staples having a relatively long leg length may be used with the cartridge 11 alone, that is, without the spacer 22. However, the same staple cartridge 11 may be utilized with staples having the same width, but with a shorter leg length, if the spacer 22 is included in the assembly.

The spacer 22 has a pair of vertical projections 24, and the surfaces 25 of the projections that are opposite the snap means of the spacer, together with the inside surface 26 of the first wall 18 serve as guide surfaces which act to guide each of several staples 28 sequentially in turn as it is ejected from the cartridge 11 by the action of the bone stapler 2. Portions of the inner surfaces of the side walls 20 may also guide each of the several staples as they are sequentially ejected from the cartridge 11 by the driver 9. When the spacer 22 is absent, the inside surface 26 and some of the inner surfaces of the side walls 20 are the only surfaces available as guide surfaces.

Due to the optional snap-fit means of the spacer 22, the means for attaching the spacer 22 to the second wall 14 is free of adhesive attachment. The guide surfaces 25 may be located substantially adjacent the sidewalls 20. By "substantially adjacent" it is meant that the surfaces 25 may be located as close as 0.008 inches plus or minus 0.008 inches from the inner surfaces of the side walls 20 for a cartridge adapted for use with staples having a width of about thirteen millimeters.

The cartridge 11 also has opposed openings 15 and 17 situated such that, when the cartridge 11 is received in the bone stapler 2, the guide surface 26 and opposed openings 15 and 17 define a portion of the stapler passageway so that the driver 9 can be moved through the opposed openings 15 and 17 between the load and eject positions. It will be appreciated that the guide surfaces defined above, namely the guide surfaces 25 of the projections 24 and the inside surface 26 are situated such that, when the cartridge 11 is received in the stapler, the guide surfaces define a portion of the stapler passageway so that the driver 9 can be moved through its opposed openings 5 and 7 and adjacent the guide surfaces between its load and eject positions in order to eject the topmost (relative to FIG. 11) of the staples in the stack 28.

Figure 5:
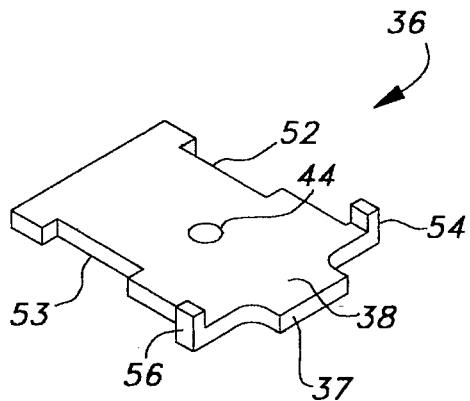
FIG. 5 is a perspective top view of a staple follower in isolation.
Figure 6:
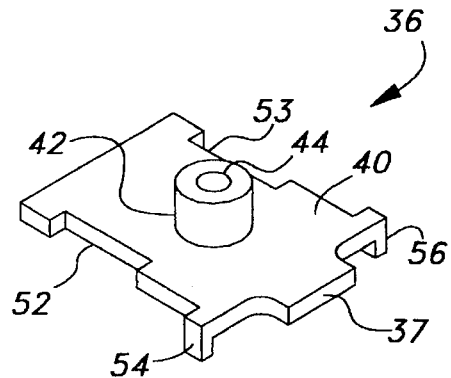
FIG. 6 is a perspective bottom view of the staple follower of FIG. 5.

The stack of staples 28 is urged into position within the passageway by a follower 36 which is movable within the case 12. Referring now to FIG. 5 and 6, the staple follower 36 is depicted in perspective views. The follower 36 is present on the side of the stack of staples 28 opposite the first wall 18. The follower 36 has a staple abutment surface 38, a spring abutment surface 40, and preferably a boss 42. The boss 42 has a hole 44 which serves as a bearing surface so that the follower 36 can be guided by a guidepost 46 which projects from the second wall 14. For example, with a cartridge adapted for use with staples having a width of about 13 millimeters, the hole may have an inner diameter of about 0.095 or 0.096 inches and the guidepost may have an outer diameter at its distal end of about 0.090 plus or minus 0.001 inches. In another embodiment of the cartridge (e.g. a cartridge adapted for use with staples having about a 7 millimeter width), the hole may have an inner diameter of about 0.085 or 0.086 inches and the guidepost may have an outer diameter at its distal end of about 0.080 plus or minus 0.001 inches. Preferably, the outer diameter of the guidepost 46 should be made of a diameter to provide a uniform thermal mass that resists warpage and that promotes uniform cooling.

The bearing surfaces 44 of the hole extend between the staple 38 and spring abutment surfaces 40 and are adapted for receiving the guidepost 46 to resist misalignment of the follower within the case. As can be seen in the Figures, all portions of the guidepost 46 are spaced from the stapler passageway, and the guidepost extends through the bearing surfaces 44. The boss 42 increases the contact area between the guidepost 46 and the follower 36 to further resist misalignment of the follower 36 within the case 12. For example, with a cartridge adapted for use with staples having a width of about 13 millimeters, the follower may have a thickness of about 0.05 inches plus or minus 0.003 inches and the boss may have a thickness of about 0.125 plus or minus 0.006 inches. For a cartridge adapted for use with staples having a width of about 7 millimeters, the follower 36 may have a thickness of about 0.05 inches plus or minus 0.003 inches and the boss 42 may have a thickness of about 0.135 plus about 0.006 inches and minus about 0.003 inches.

A spring 48 is provided for biasing the follower 36 and the stack of staples 28 toward the first wall 18 and into position where individual staples may be sequentially ejected. The spring 48 is positioned about the boss 42. The interaction of the boss 42 and the guidepost 46 helps to resist misalignment of the follower within the case 12. Preferably, the second wall 14, (which might be said to be a cover opposite the first wall 18) has a recess 50 adapted to receive the boss 42 of the follower 36 and a portion of the spring 48. The spacer 22 is preferably spaced from the spring 48 and the boss 42. Also, preferably, the spring may be constructed from any suitable sterilizable material, such as, but not limited to stainless steel.

Figure 3:
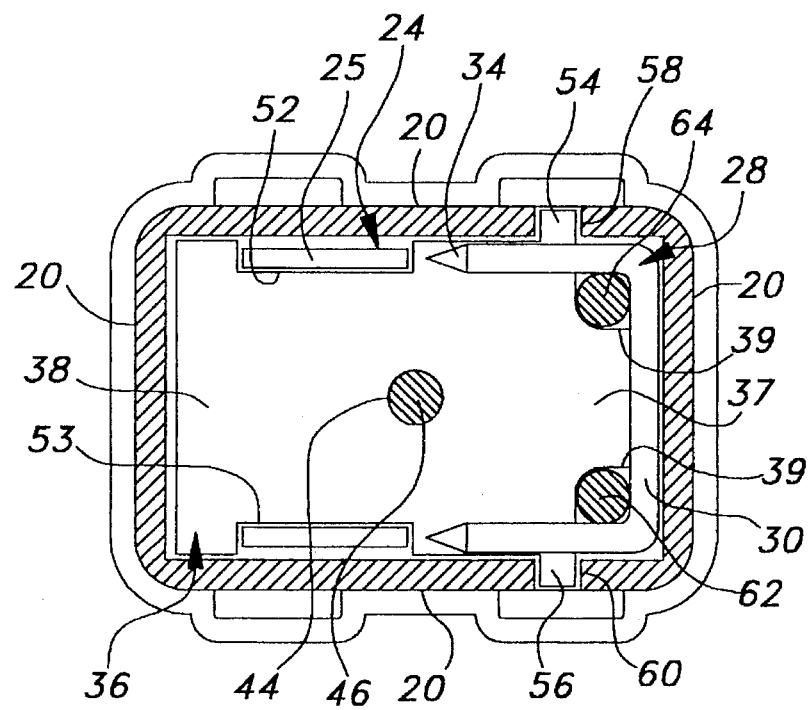
FIG. 3 is a cross-section view taken approximately along section lines 3—3 in FIG. 2.

Referring now to FIG. 3, a cross-section view of the cartridge 11 is depicted. In this view it can be seen that the follower 36 extends substantially the entire internal length of case 12, with travel slots 52 and 53 provided so that the projections 24 on spacer 22 can extend upwards (in FIG. 2, 4, 9 and 11) past the follower 36 to guide the ejection of staples 28. It can be appreciated that the central position of guidepost 46 relative to follower 36 provides an even support for the lifting of the staples 28 sequentially into position for ejection, tending to reduce any opportunity for the staples to jam, or even for the follower to tilt within the case.

As best seen in FIG. 3, the follower 36 includes a guide tab 37. Preferably, the guide tab 37 abuts a central portion 30 of the bottommost staple in the stack of staples to support the stack of staples and to resist misalignment of the follower within the case. Further, the guide tab 37 helps ensure that the central portion 30 of the staple to be driven by the driver 9 clears the top portion of posts 62 and 64 (see FIG. 4).

The case 12 includes structure comprising a guide channel 39 adapted to receive the guide tab 37 to provide stability and to restrict misalignment of the follower 36 within the case 12. Preferably, the guide channel 39 is formed by restraining posts 62 and 64 which are described in greater detail below.

The stability of the follower 36 is further enhanced by providing two travel tabs 54 and 56 which extend from the follower 36 into a pair of complementary alignment channels 58 and 60 within the side walls 20 of the case 12. Alternatively, the alignment channels could be formed by a pair of posts projecting from the side walls 20 or the second wall 14. The travel tabs 54 and 56 further serve to prevent the staple driver 9 from driving the follower 36 out through the outlet 17 of the cartridge 11. As seen in FIG. 5, travel tabs 54 and 56 extend slightly upwards beyond the thickness of the follower 36. In this manner, after all of the staples 28 have been ejected from the case 12, the tabs 54 and 56 come in contact with surfaces 1 (FIG. 11) on the surfaces of the stapler 2 that are adapted to receive the cartridge 11. As a result, the tabs 54 and 56 prevent the follower 36 from rising to a position where the staple driver 9 could contact it.

Restraining posts 62 and 64 are provided, which restrain all the staples 28 except the staple which is in the topmost position (relative to FIG. 4), so that the driver 9 in the bone stapler 2 does not accidently simultaneously drive two staples toward the outlet 17. The restraining posts 62 and 64 also assist in maintaining alignment of the staples within the cartridge 11. A stiffening rib 63 strengthens the posts 62 and 64 and resists thermal deformation of the part shown in FIG. 12 after molding.

Figure 4:
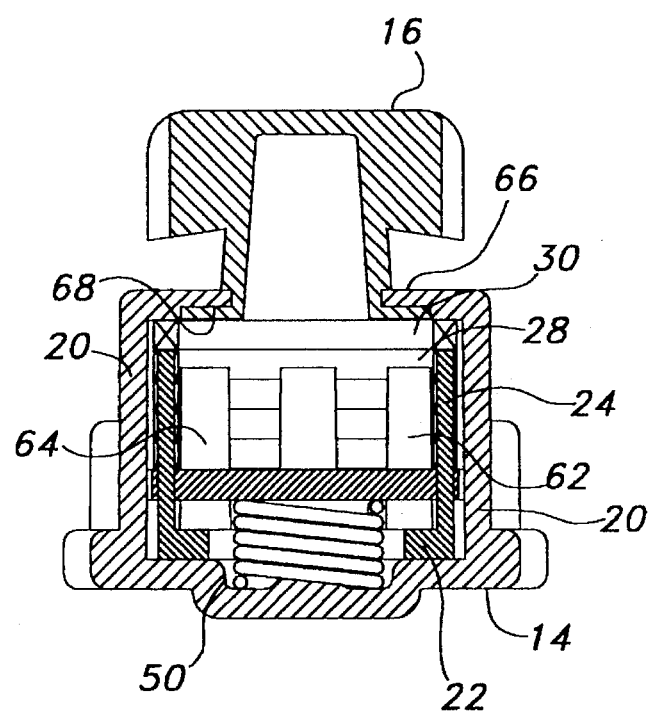
FIG. 4 is a cross-section view taken approximately along section lines 4—4 in FIG. 2.

Referring now to FIG. 4, there is shown retaining means for releasably retaining the case 12 in engagement with the stapler housing 3. The retaining means comprises the locking member 16 with a groove 66 which is sized to provide a captured groove fit within a hole 68 in the first wall 18 of the case 12. In this manner, the locking member 16 is able to pivot about an axis relative to the case 12. To attach the cartridge to the stapler 2, the locking member 16 is threaded through a correspondingly shaped hole in the housing of the stapler 2, and then pivoted to firmly attach the cartridge 11 in the stapler 2. The locking member 16 is thus able to serve as a retaining means for releasably retaining the case 12 in engagement with the stapler housing 3, in the manner generally disclosed in U.S. Pat. No. 4,569,469.

Figure 9:
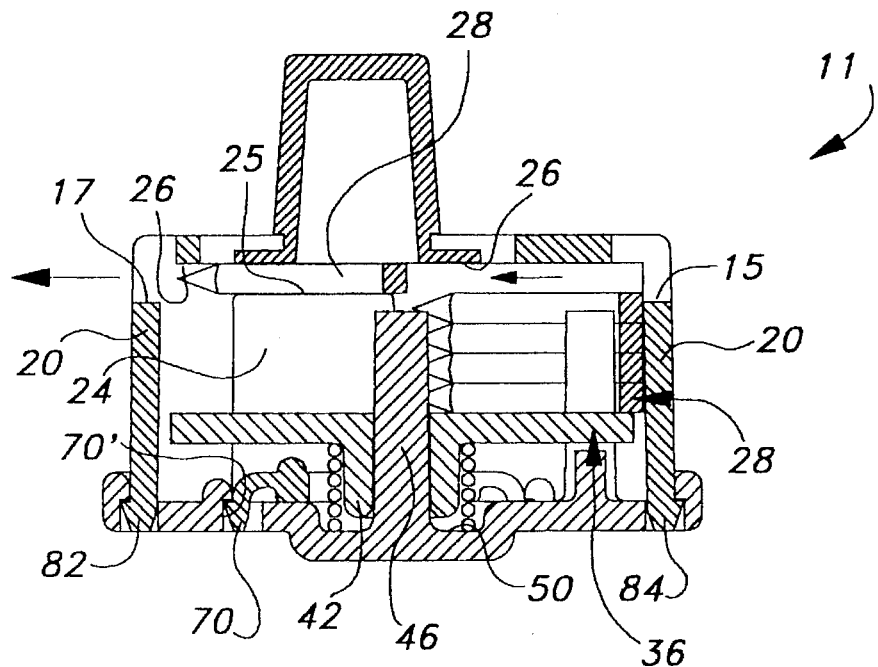
FIG. 9 is a cross-section side view of a cartridge which illustrates the ejection of a staple while the staple is supported by an optional spacer.
Figure 10:
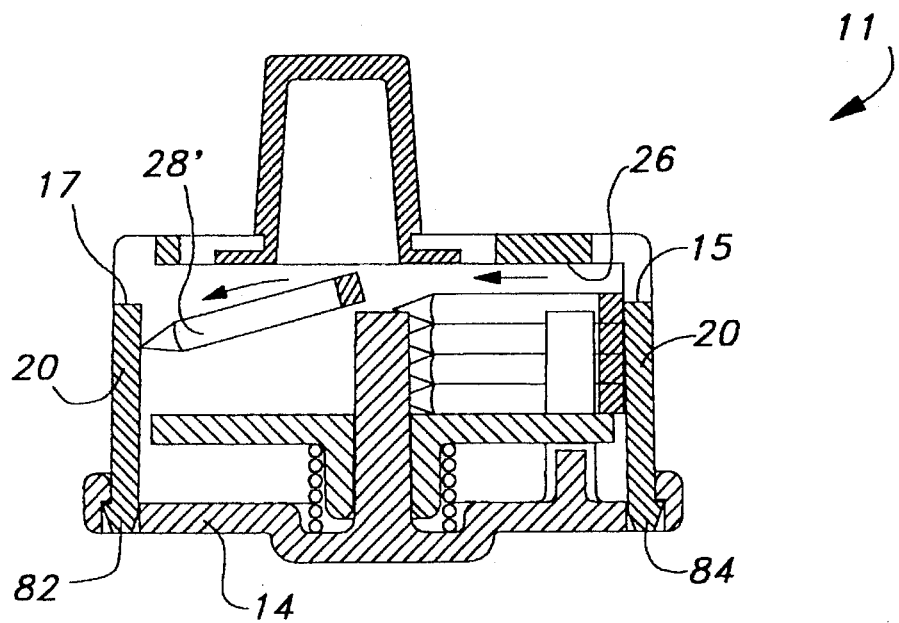
FIG. 10 is a cross-section side view similar to FIG. 9, except that the spacer according to the present invention is removed, and which further illustrates a potential undesirable result should the spacer be absent.

Referring now to FIG. 9, there is shown a cross-section side view of a cartridge 11 where a staple 28' is being ejected while being supported by a spacer 22. In this view, the arrows show the movement of a staple 28' from the top of the stack toward a staple exit 17 during use. The driver 9 from the stapler 2 which is accomplishing this movement is omitted for visual clarity. The staple 28' moves robustly within the cartridge 11, securely supported between the guide surfaces 25 of projections 24 and the inside surface 26 of the first wall 18. Contrast this to the situation depicted in FIG. 10, where the lack of a spacer according to the present invention has precipitated a staple jam within the cartridge 11.

ASSEMBLY

Alternatively, the present invention may be described as a method of making a cartridge comprising the steps of: (1) providing a case 12 comprising a first wall 18 and side walls 20 projecting from the first wall, inner guide surfaces, and openings 15 and 17; (2) providing a stack of staples 28; (3) providing a follower 36 on the side of the stack of staples 28 opposite the first wall 18, (4) mounting the follower 36 so that it is movable within the case 12 with the stack of staples 28, (5) providing a spring 48 for biasing the follower 36 and the stack of staples 28 toward the first wall 18; (6) providing a spacer 22 having guide surfaces 25 for guiding a staple through one of the opposed openings (e.g. 17), and (7) attaching the spacer 22 to the case 12 without the use of an adhesive. Preferably, step (7) includes the step of attaching the spacer 22 to the case 12 in a position such that the guide surfaces 25 are substantially adjacent a side wall 20. More preferably, step (7) includes the step of attaching the spacer 22 to a second wall 14 in a first subassembly, and then attaching the first assembly to a component which forms the first wall 18 and side walls 20.

Figure 17:
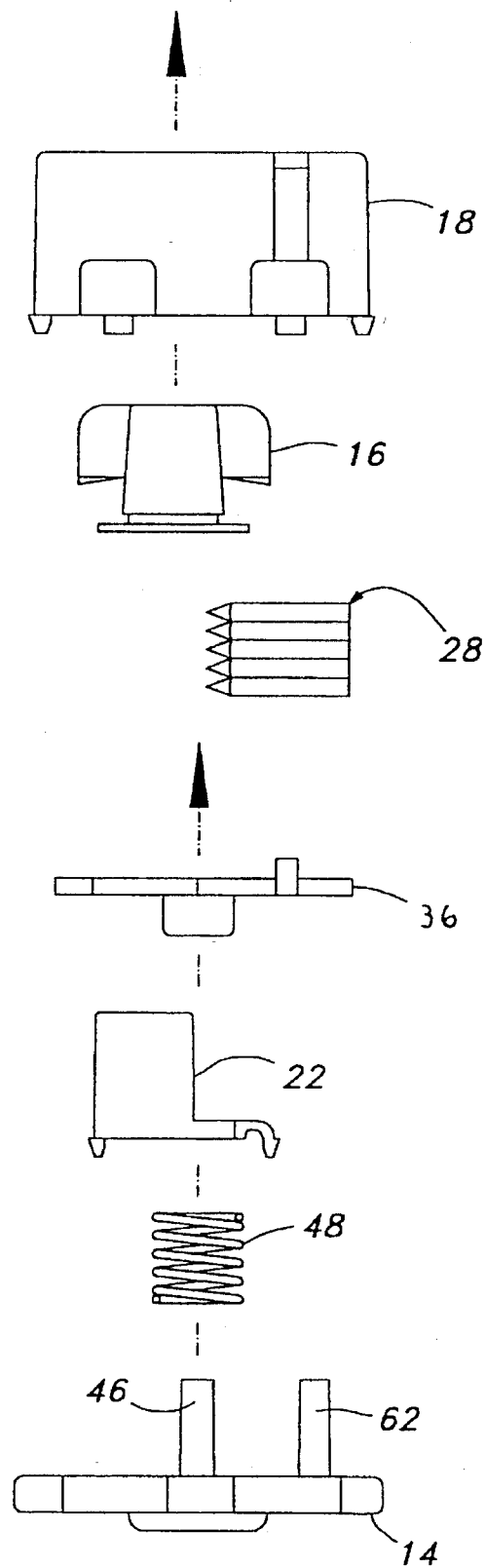
FIG. 17 schematically illustrates the assembly of a staple cartridge assembly according to the present invention.

FIG. 17 schematically illustrates an example of the method set forth above. Preferably, as a first subassembly, the spacer 22 is attached to the component forming the second wall 14 by virtue of a snap-fit. A second subassembly comprises the locking member 16 being snap-fit to the component which forms the first wall 18 and side walls 20. Finally, the follower 36, stack of staples 28 and spring 48 are placed between the first and second subassemblies and then the first and second subassemblies are snap-fit together. Again, it should be noted that by "snap-fit means", what is meant is a mode of clasping which involves a portion, such as a hook, on one of the parts to be clasped which, when pressed against a portion, such as a recess on the other part, is capable of, and indeed adapted for, a resilient deflection which allows the parts to interact and thereafter resist being separated.

Figure 7:
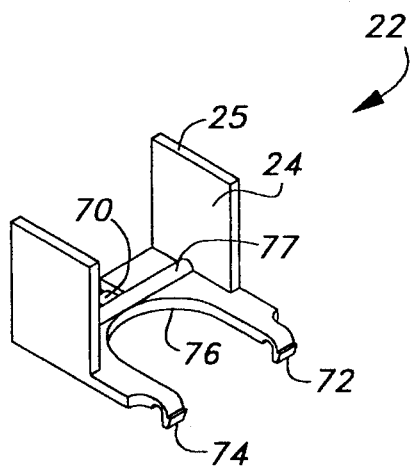
FIG. 7 is a perspective top view of an optional spacer in isolation.

All of the snap-fits are preferably accomplished by a plurality of complementary pairs of hooks and recesses adapted to snap into engagement with each other. Referring now to FIG. 7, a perspective view of a spacer 22 is depicted in isolation. The spacer 22 can be seen to have three hooks 70, 72 and 74, which as will be noted below with more particularity, interlock with complementary receptacles 70', 72' and 74' on second wall 14. This interaction allows the cartridge 11 (with a spacer) to be manufactured without the use of solvent welding and the concomitant disadvantages discussed above.

The spacer 22 has a peripheral portion 76 to allow for optimum positioning of the guidepost 46. The peripheral portion is shaped to afford a substantially centered position of the spring 48, guidepost 46, follower 36 and recess 50 with the case 12. A stiffening rib 77 is provided to retain a vertical orientation (relative to FIG. 4) of the projections 24 after being ejected from an injection mold. The added material of stiffening rib 77 assists in equalizing the amount of material in the projections 24 and the rest of the spacer 22. By adding material to help provide a more uniform thermal mass, heat transfer is more uniform as the spacer 22 ejects from the mold and cools.

Figure 8:
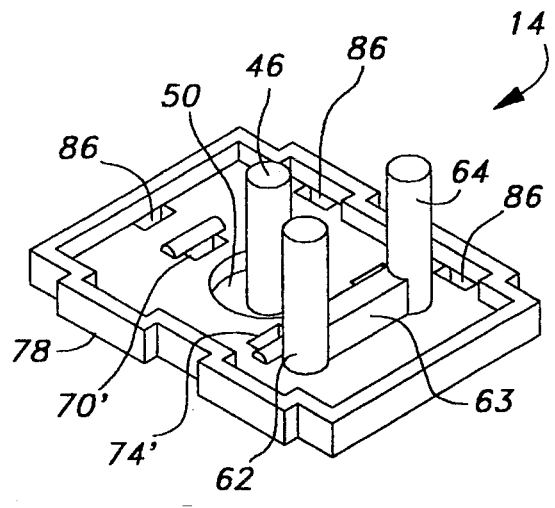
FIG. 8 is a perspective top view of a component for providing a second wall illustrated in isolation.

Referring now to FIG. 8, a perspective top view of a second wall 14 is seen in isolation. Along the periphery of the second wall 14 are seen four niches 78 which seat four complementary reinforcing panels 80 (seen in FIG. 1) on the side walls 20 of the case 12. The panels 80 and niches 78 afford a stronger finished assembly. Such assembly is accomplished as a snap-fit by fitting six hooks (82 and 84 on the side walls 18 of the case 12, as seen in FIG. 2 are typical) into six complementary receptacles 86 in the second wall 14. Second wall 14 also has receptacles 70', 72' and 74' which interact with hooks 70, 72, and 74 to provide a snap-fit connection between the second wall 14 and the spacer 22.

EXAMPLE

Preferred construction of the cartridge disclosed above is achieved when the materials used to construct the case 12 are sturdy enough to withstand the forces placed on the assembly by the stapler, yet tough, resilient and flexible enough to hook properly at the snap-fit connections. Optical clarity, so that the user of the cartridge can determine at a glance how many staples remain to be used is also desirable. Injection moldings from a polycarbonate, commercially available as Makkrolon FCR-2458, color 1117, from Mobay of Pittsburgh, Pa., are suitable for construction of the cartridge 11. The spring is conveniently prepared from type 302 stainless steel, passivated after coiling. The staples are constructed from titanium 6-4 ELI.

Figure 14:
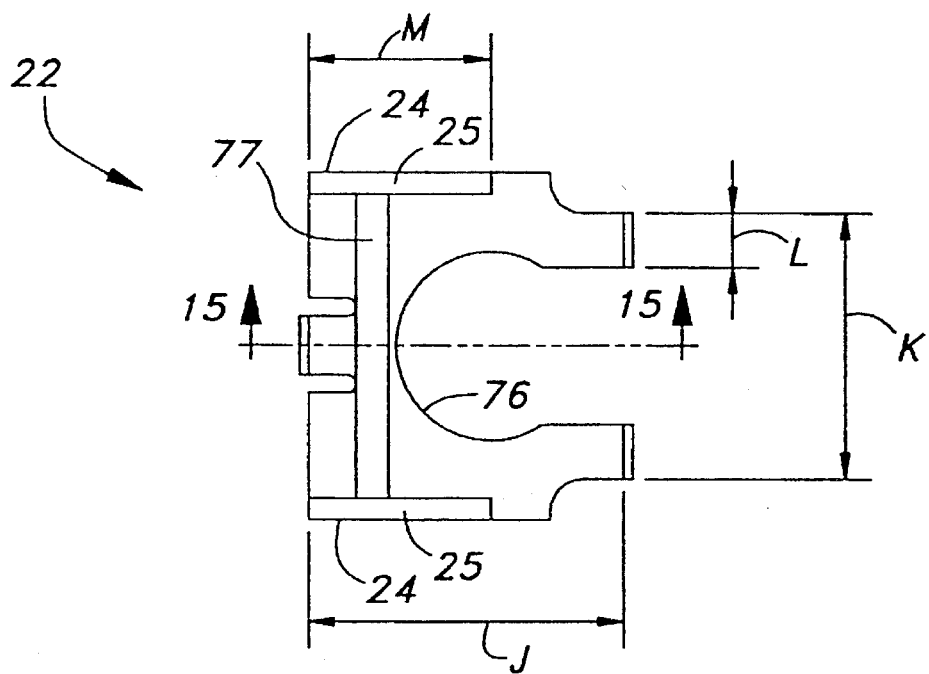
FIG. 14 is an enlarged top view of the spacer of FIG. 7.
Figure 15:
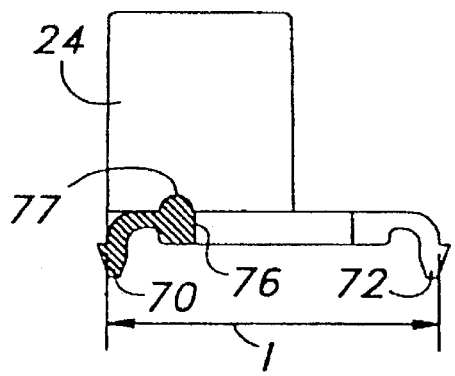
FIG. 15 is a sectional view taken approximately along lines 15—15 of FIG. 14.
Figure 16:
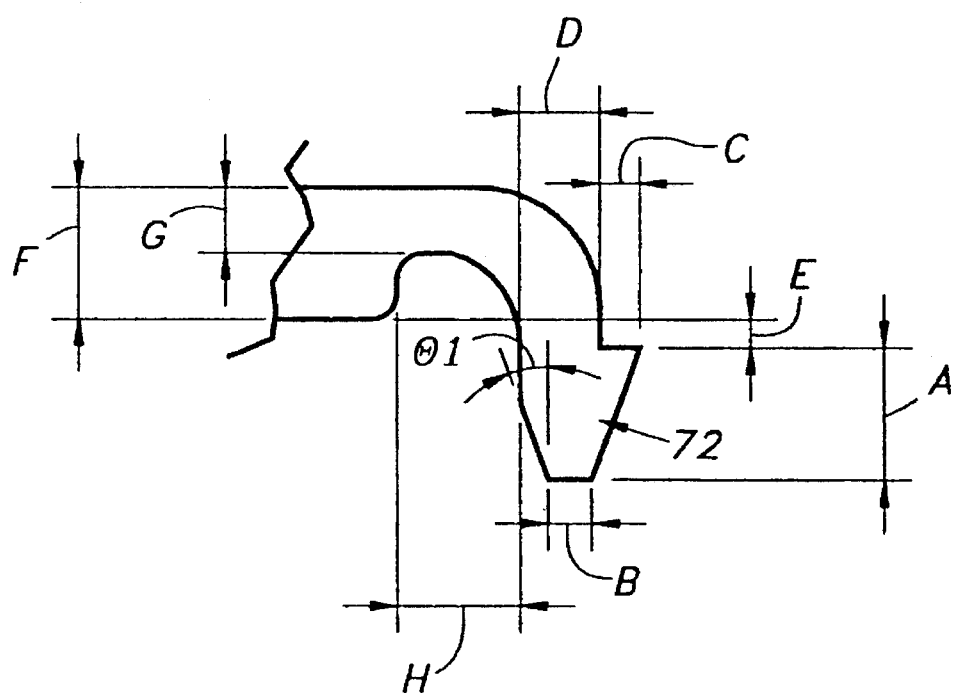
FIG. 16 is a detail view of a hook forming a portion of a snap fit means of the present invention.

FIGS. 14–16 illustrate preferred dimensions A through M for the snap-fit for the spacer 22 for use in a cartridge for staples with central portion widths of about 13 millimeters. Table 1 illustrates preferred measurements for a spacer according to example 1:

TABLE 1

| Dimension | Length (+ or − 0.003 inches unless stated otherwise) |
|---|---|
| A | 0.047 |
| B | 0.015 |
| C | 0.015 |
| D | 0.030 |
| E | 0.003 + or − 0.001 |
| F | 0.050 |
| G | 0.030 |
| H | 0.050 |
| I | 0.495 |
| J | 0.51 + or − 0.005 |
| K | 0.460 |
| L | 0.100 |
| M | 0.270 + or − 0.005 |
| theta 1 | 20 (degrees) |

The dimensions for the snap-fit between the second wall 14 and the side walls 20 may be substantially the same as the dimensions for the snap-fit between the spacer 22 and the second wall 14. The shape of dimensions A, C, I, and L are similar to the shapes shown in FIGS. 14–16. Preferred measurements for such a snap-fit are set forth in Table 1A:

TABLE 1A

| Dimension | Length (+ or − 0.003 inches unless stated otherwise) |
|---|---|
| A | 0.050 |
| C | 0.015 |
| I | 0.918 + or − 0.011 inches |
| L | 0.100 |

Note the dimension I of the spacer (FIG. 15) is similar to the distance between the snaps of the cartridge in the lengthwise direction.

Figure 12:
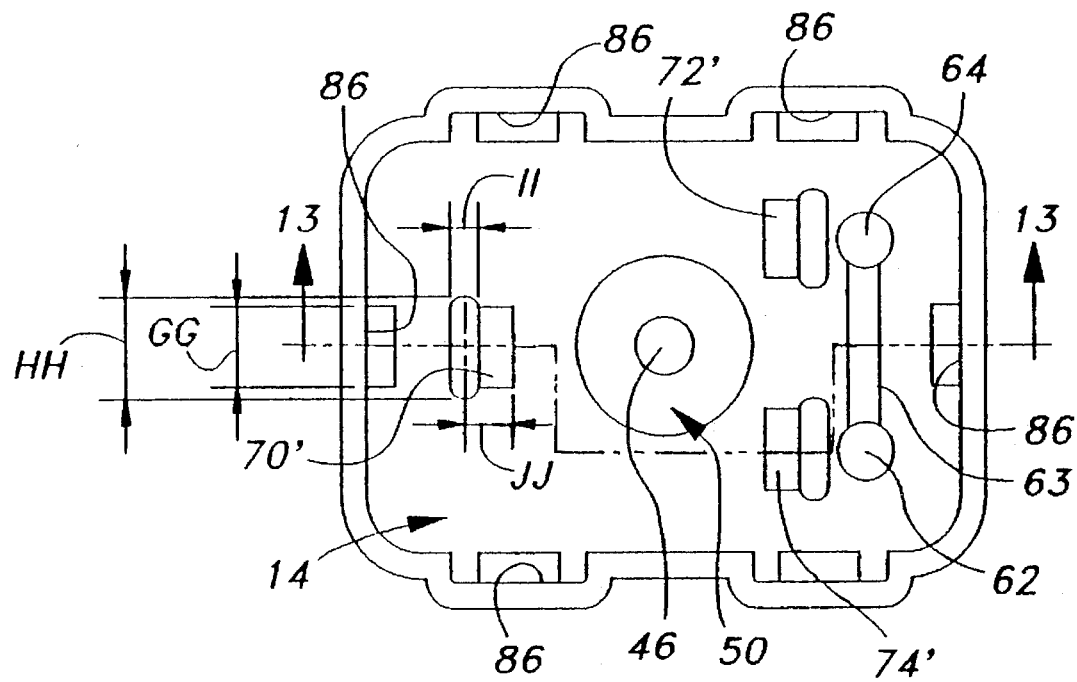
FIG. 12 is an enlarged top view of the component of FIG. 8.
Figure 13:
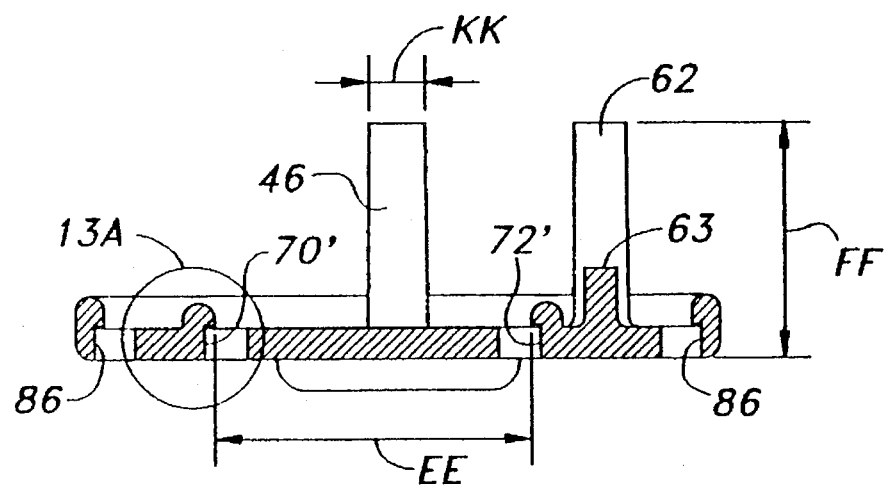
FIG. 13 is a sectional view taken approximately along lines 13—13 of FIG. 12.
Figure 13A:
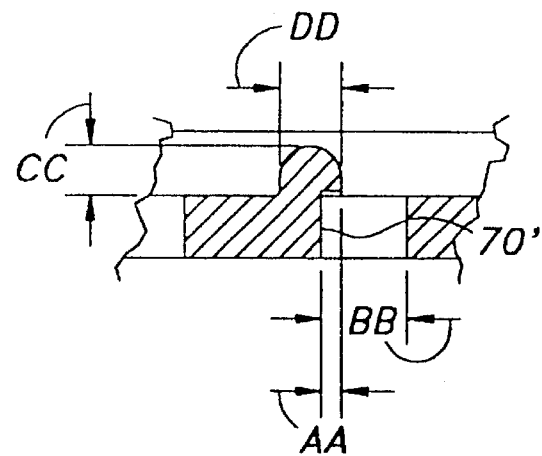
FIG. 13A is a detail view of approximately the circled portion of FIG. 13.

FIGS. 12, 13 and 13A illustrate dimensions AA–KK which are preferred for the component used to form the second wall 14 designed for use with the spacer 22 of Table 1. Table 2 illustrates preferred measurements for the component used to form the second wall 14 according to example 1:

TABLE 2

| Dimension | Length (+ or − 0.005 inches unless noted otherwise) |
|---|---|
| AA | 0.025 |
| BB | 0.070 |
| CC | 0.040 |
| DD | 0.050 |
| EE | 0.495 + or − 0.002 |
| FF | 0.320 |
| GG | 0.12 |
| HH | 0.18 + or − 0.01 |
| II | 0.050 |
| JJ | 0.045 + or − 0.01 |
| KK | 0.090 + or − 0.001 |

As various changes could be made in the above constructions and methods without departing from the scope of the invention, it is intended that all matter contained in the above description be interpreted as illustrative and not in a limiting sense.

We claim:

1. A cartridge adapted to be received by a stapler for driving staples, which stapler comprises a stapler housing having a stapler passageway extending from an inlet opening to an outlet opening; a driver having a staple driving end portion adapted to engage a staple, said driver being mounted for movement between a load position with the driver spaced from the inlet opening so that one of the staples may be positioned in the stapler passageway and an eject position;

said cartridge comprising:

a case comprising a first wall and side walls projecting from said first wall, inner guide surfaces, opposed openings situated such that, when the cartridge is received by the stapler, the guide surfaces and opposed openings define a portion of said stapler passageway so that said driver can be moved through said opposed openings between said load and eject positions;

a stack of staples;

a guidepost spaced from said stapler passageway;

a follower on the side of said stack of staples opposite said first wall and movable within said case with said stack of staples, a spring for biasing said follower and said stack of staples toward said first wall;

said follower having a staple abutment surface adapted to engage a staple in the stack of staples, a spring abutment surface adapted to engage said spring, and bearing surfaces extending between the staple abutment surface and spring abutment surface for receiving the guidepost to resist misalignment of the follower within the case; and retaining means for releasably retaining said case in engagement with said stapler housing.

2. A cartridge according to claim 1 wherein said follower further comprises a boss having surfaces forming a portion of the bearing surfaces to increase contact area between the guidepost and the follower to further resist misalignment of the follower within the case.

3. A cartridge according to claim 2 wherein said spring is positioned about said boss, and said cartridge including a second wall opposite said first wall, said second wall including a recess adapted to receive the boss of said follower and a portion of said spring.

4. A cartridge according to claim 3 wherein the cartridge further includes a spacer, wherein said spacer is spaced from said spring and said boss.

5. A cartridge according to claim 1 wherein the cartridge further includes a spacer having guide surfaces substantially adjacent said sidewalls for guiding a staple through one of said opposed openings.

6. A cartridge according to claim 5 wherein the cartridge further includes a second wall opposite said first wall, and snap-fit means for attaching said spacer to said second wall, said snap-fit means being free of adhesive.

7. A cartridge according to claim 1 wherein said follower includes a guide tab for abutting a staple in the stack of staples, the case includes structure comprising a guide channel adapted to receive said guide tab to restrict misalignment of said follower within said case.

8. A cartridge according to claim 7 wherein the cartridge includes a second wall opposite said first wall, and the guide channel is formed by a pair of posts projecting from said second wall and spaced from said stapler passageway.

9. A cartridge according to claim 6 wherein said snap-fit means for attaching said spacer to said second wall comprises a plurality of complementary pairs of hooks and recesses adapted to snap into engagement with each other.

10. A cartridge adapted to be received by a stapler for driving staples, which stapler comprises a stapler housing having a stapler passageway extending from an inlet opening to an outlet opening; a driver having a staple driving end portion adapted to engage a staple, said driver being mounted for movement between a load position with the driver spaced from the inlet opening so that one of the staples may be positioned in the stapler passageway and an eject position;

said cartridge comprising:

a case comprising a first wall and side walls projecting from said first wall, inner guide surfaces, openings situated such that, when the cartridge is received by the stapler, the guide surfaces and openings define a portion of said stapler passageway so that said driver can be moved through said openings between said load and eject positions;

a stack of staples;

a guidepost spaced from said stapler passageway;

a follower on the side of said stack of staples opposite said first wall and movable within said case with said stack of staples, a spring for biasing said follower and said stack of staples toward said first wall;

said follower having staple abutment surface adapted to engage a staple in the stack of staples, and a spring abutment surface adapted to engage said spring, and bearing surfaces extending between the staple abutment surface and the spring abutment surface for receiving the guidepost to resist misalignment of the follower within the case;

a spacer-having guide surfaces for guiding a staple through one of said openings, snap fit means for attaching the spacer to the case; and retaining means for releasably retaining said case in engagement with said stapler housing.

11. A cartridge according to claim 10 wherein said follower further comprises a boss having surfaces forming a portion of said bearing surfaces to increase contact area between the guidepost and the follower to further resist misalignment of the follower within the case.

12. A cartridge according to claim 11 wherein said spring is positioned about said boss, and said cartridge including a second wall opposite said first wall, said second wall including a recess adapted to receive the boss of said follower and a portion of said spring.

13. A cartridge according to claim 10 wherein the cartridge includes a second wall opposite said first wall, and the snap fit means attaches the spacer to the second wall in a location such that the guide surfaces of the spacer are substantially adjacent said sidewalls.

14. A cartridge according to claim 10 wherein said follower includes a guide tab for abutting a staple in the stack of staples, and the case includes structure comprising a guide channel for receiving said guide tab to restrict misalignment of said follower within said case.

15. A cartridge according to claim 14 wherein the cartridge includes a second wall opposite said first wall, and the guide channel comprises a pair of posts projecting from said second wall and spaced from said stapler passageway.

16. A cartridge according to claim 10 wherein said snap-fit means for attaching said spacer to said case comprises a plurality of complementary pairs of hooks and recesses adapted to snap into engagement with each other.

17. In combination, a stapler for driving staples, and a cartridge adapted for use in the stapler, each of the staples comprising a central portion having a pair of ends and a leg portion projecting from each of said ends, said leg portions having distal ends;

the stapler comprising a stapler housing having a passageway extending from an inlet opening to an outlet opening, the passageway being adapted to guide a single staple moved from the inlet to the outlet opening with the distal ends of its legs leading, a driver having a staple driving end portion adapted to engage a staple, said driver being mounted for movement between a load position with the driver spaced from the inlet opening so that one of the staples may be positioned in the passageway and an eject position at which the staple driving end portion of the driver pushes the staple out the outlet opening, and drive means adapted to be manually activated for propelling the driver along the passageway from the load to the eject position to move the staple from the inlet to the outlet opening, the stapler housing including surfaces adapted to receive said cartridge;

said cartridge comprising:

a case comprising a first wall and side walls projecting from said first wall, inner guide surfaces, opposed openings situated such that, when the cartridge is received in the stapler, the guide surfaces and opposed openings define a portion of said stapler passageway so that said driver can be moved through said opposed openings between said load and eject positions;

a stack of staples;

a guidepost spaced from said stapler passageway;

a follower on the side of said stack of staples opposite said first wall and movable within said case with said stack of staples, a spring for biasing said follower and said stack of staples toward said first wall;

said follower having a staple abutment surface adapted to engage a staple in the stack of staples, a spring abutment surface adapted to engage said spring, and bearing surfaces extending between the staple abutment surface and spring abutment surface for receiving the guidepost to resist misalignment of the follower within the case; and retaining means for releasably retaining said case in engagement with said stapler housing.

18. A combination according to claim 17 wherein the cartridge further includes a spacer having guide surfaces substantially adjacent said sidewalls for guiding a staple through one of said opposed openings.

* * * * *